United States Patent [19]

Maurer et al.

[11] 4,377,699

[45] Mar. 22, 1983

[54] 5-CHLORO-INDOLE PREPARATION

[75] Inventors: Manfred Maurer, Kirchheim; Winfried Orth, Hassloch; Werner Fickert, Mannheim, all of Fed. Rep. of Germany

[73] Assignee: Rutgerswerke Aktiengesellschaft, Frankfurt am Main, Fed. Rep. of Germany

[21] Appl. No.: 300,607

[22] Filed: Sep. 9, 1981

[30] Foreign Application Priority Data

Sep. 19, 1980 [DE] Fed. Rep. of Germany ....... 3035403

[51] Int. Cl.$^3$ ............................................ C07D 209/08
[52] U.S. Cl. .................................. 548/469; 548/490; 548/491
[58] Field of Search .................... 260/326.11 R, 319.1

[56] References Cited

U.S. PATENT DOCUMENTS 3,184,466  5/1965  Hennig et al. ............. 260/326.11 R
4,005,206  1/1977  Gaignault et al. .................. 424/263

FOREIGN PATENT DOCUMENTS 1123668  2/1962  Fed. Rep. of Germany.
1143823  5/1968  Fed. Rep. of Germany.
2618152  6/1977  Fed. Rep. of Germany.
2719294  11/1977 Fed. Rep. of Germany.
2738646  2/1978  Fed. Rep. of Germany.

OTHER PUBLICATIONS

Mazza et al. (Farmaco, Ed. Sci., vol. 32 (1) (1977), p. 54.
Japanese Patent Appln. Serial No. 77,108,969 filed in 1977 [Chem. Abs., vol. 88 (1978), p. 136451x].
Huisgen et al., [Chem. Ber., vol. 93 (1960), p. 1496–1506].
Ikan et al. [Israel J. Chem., vol. 2 (2) (1964), p. 37–42].
Thesing et al. [Chem. Ber., vol. 95(1962), p. 2205].
Gall et al., [J. Org. Chem., vol. 20 (1955), p. 1538].
British Patent 919,864 [Chem. Abstracts, vol. 59, (1963), Col. 8710].
Japanese Patent Appln. 69-27967 [Chem. Abstracts vol. 72, (1970), p. 43446d].
Terent'ev et al., [Proc. Acad. Sci. USSR, vol. 118(2) (1958), p. 49–52].
French Patent 1,576,807 [Chem. Abs. vol. 72(1970), p. 121360n].
Bader et al., [J.A.C.S., vol. 83 (1961), p. 3319].
Hunt et al., [J. Chem. Soc., (C) (1966), p. 344–345].
Bakke [Acta, Chem. Scand., vol. 28(1974) No. 1, p. 134].
Imai et al., [Org. Chem., vol. 42(3) (1977), p. 431].
Imai et al., [Chemistry Letters, (1976), p. 855–856, 655–656].

*Primary Examiner*—Donald G. Daus
*Assistant Examiner*—M. C. Eakin
*Attorney, Agent, or Firm*—Hammond & Littell, Weissenberger and Muserlian

[57] ABSTRACT

An improved process for the preparation of 5-chloro-indole comprising reacting indoline in a chlorine-inert organic solvent with an acylating agent of an organic carboxylic acid to obtain the corresponding 1-acyl-indoline, reacting the latter in the presence of water and a basic agent with chlorine to form 5-chloro-1-acyl-indoline, subjecting the latter to saponification to obtain 5-chloro-indoline and reacting the latter in a water-immiscible organic solvent by heating with an aromatic nitrocompound in the presence of a finely powdered ruthenium catalyst to form 5-chloro-indole in excellent yields.

10 Claims, No Drawings

5-CHLORO-INDOLE PREPARATION

STATE OF THE ART

DOS Nos. 2,618,152, 2,719,294 and 2,738,646 describe the use of 5-chloro-indole as an antidepressant, anti-emetic agent and anti-parkinson agent and U.S. Pat. No. 4,005,206 and German Pat. No. 1,143,823 describe the use of 5-chloro-indole as a starting material for 5-chloro-tryptamine which is an intermediate for the synthesis of tranquilizers and anti-hypertension agents. Intermediates 5-chloro-indoline and 5-chloro-1-acyl-indolines are also valuable starting materials for the preparation of other medicaments and 1-acetyl-5-chloro-indoline has phytotoxic activity as taught by Mazza et al. [Farmaco, Ed. Sci., Vol. 52 (1) (1977), p. 54[. However, direct synthesis of 5-chloro-indole by the steps of 1-acyl-indoline, 1-acyl-5-chloro-indoline and 5-chloro-indoline is not known.

Japanese Patent Application Serial No. 77-108,969 filed in 1977 [Chem. Abs., Vol. 88 (1978), p. 136451x] describes the preparation of indoline and benzene ring-substituted indolines by heating corresponding substituted 2-(o-aminoaryl)-ethanols up to 250° C. and Huisgen et al. [Chem. Ber., Vol. 93 (1960), p. 1496–1506] describe the preparation of indoline derivatives by cyclizing arine intermediates. Ikan et al. [Israel J. Chem., Vol. 2 (2) (1964), p. 37–42] describes the preparation of 5-chloro-indoline from indoline in several stages by nitrating the N-acetyl-indoline in the 5-position, reducing the nitro group to an amino group and subjecting the latter to exchange with chlorine by the Sandmeyer reaction followed by saponification of the acetyl group for a 35% yield of 5-chloro-indoline.

Gall et al. [J. Org. Chem., Vol. 20 (1955), p. 1538] describes the direct bromination of 1-acetyl-indoline in glacial acetic acid with bromine followed by saponification to obtain 5-bromo-indoline in 85% yield but attempts to repeat the process with chlorine results in only about a 45% yield of 5-chloro-1-acetyl-indoline. The latter result is not surprising in view of references such as Thesing et al. [Chem. Ber., Vol. 95 (1962), p. 2205], German Pat. No. 1,123,668, British Pat. No. 919,864 and the Chemistry of Heterocyclic Compounds, Vol. 25, Indoles, part II, Wiley Interscience, New York, London, Sidney, Toronto, 1972 p. 129 which teach that the reaction of N-acetylated-indoline-2-sulfonates in glacical acetic acid with chlorine, hypochlorous acid or alkali metal hypochlorites results in a variety of chlorinated products including 5- and 7-chloro compounds. Japanese Patent Application Ser. No. P 69-27967 (1969) teaches that these difficulties may be avoided by reacting 1-acetyl-indoline with N-chlorosuccinimide in carbon tetrachloride.

All these known methods are unsatisfactory for the commercial production of 5-chloro-1-acyl-indolines and/or 5-chloro-indoline by saponification of the acyl group due to poor yields and the use of rather expensive reagents such as N-chlorosuccinimide.

Ikan et al. [Israel J. of Chemistry, Vol. 2 (1964), p. 37–42] and Terent'ev et al. [Proc. Acad. Sci. USSR, Vol. 118 (2) (1958), p. 49–52] describe the dehydration of 5-chloro-indoline with chloranil to obtain 5-chloro-indole but due to the expense of chloranil, the process is not commercially feasible. French Pat. No. 1,576,807, DOS No. 1,770,977, Chem. Abs., Vol. 72 (1970), p. 121360n and Bader et al. [J.A.C.S., Vol. 83 (1961), p. 3319] tried to avoid this difficulty with partial success by heating indoline and its derivatives to high temperatures in the presence of palladium, platinum of Raney nickel catalysts, sometimes in the presence of a hydrogen acceptor. For example, indoline can be dehydrated at 100 to 150° C. in aromatics with a good yield of indole with hydrogen in the presence of finely divided palladium. Hunt et al. [J. Chem. Soc., (C) (1966), p. 344–345] teach reacting 5-methoxy-indoline in refluxing mesitylene in the presence of palladized carbon to obtain a 90% yield of 5-methoxy-indole.

Bakke [Acta, Chem. Scand., Vol. 28 (1974) No. 1, p. 134] describes reacting 4-chloro-indoline and 6-chloro-indoline with palladized carbon in a refluxing aromatic to obtain yields of 52% of 4-chloro-indole and 73% of 6-chloro-indole, respectively. However, the said process can not be used to convert 5-chloro-indoline to 5-chloro-indole since hydrogen and chlorine are both removed resulting in resinification to form undefined and non-distillable residues.

Org. Chem., Vol. 42 (3) (1977), p. 431 and Chemistry Letters, 1976, p. 655–656 describe the reaction of indoline in an aromatic solvent with nitrocompounds such as nitrobenzene in the presence of platinum group metal salts such as halides of rhodium, palladium or ruthenium at 100° C. to form indole, water and the amino compound corresponding to the starting nitrocompound. However, the presence of the platinum group metal salts causes to various degrees the removal of any halogen substituent and bases as they are formed increase this effect even more (Chemistry Letters, 1974, p. 855–856). Moreover, the solubility of the platinum group metal salts makes their recovery and subsequent reuse difficult and complicated.

OBJECTS OF THE INVENTION

It is an object of the invention to provide an economical process for the production of 5-chloro-indole starting from indoline in high yields.

It is another object of the invention to form 5-chloro-indole from indoline in a minimum number of steps in a commerically feasible process.

These and other objects and advantages of the invention will become obvious from the following detailed description.

THE INVENTION

The novel process of the invention for the preparation of 5-chloro-indole comprises reacting indoline in a chlorine-inert organic solvent with an acylating agent of an organic carboxylic acid to obtain the corresponding 1-acyl-indoline, reacting the latter in the presence of water and a basic agent with chlorine to form 5-chloro-1-acyl-indoline, subjecting the latter to saponification to obtain 5-chloro-indoline and reacting the latter in a water-immiscible organic solvent by heating with an aromatic nitrocompound in the presence of a finely powdered ruthenium catalyst to form 5-chloro-indole.

The acylating agent is preferably the carboxylic acid halide or acid anhydride with a molar ratio of indoline to acylating agent of 1:1 to 1.5 and the preferred reaction temperature is 0° to 60° C. The chlorination of the resulting 1-acyl-indoline after treatment with water in the presence of a base is effected with a molar ratio of 1-acyl-indoline to chlorine of 1:1 to 1.2 preferably at 0° to 60° C., most preferably 20° to 30° C. The organic solvent is then preferably distilled off and the 5-chloro-1-acyl-indoline is crystallized from a lower-alkanol of 1 to 6 carbon atoms which is unexpected in view of the state of the art.

Examples of suitable carboxylic acids of 1 to 18 carbon atoms for the process are alkanoic acid such as formic acid, acetic acid, propionic acid, butyric acid, isobutyric acid, valeric acid, isovaleric acid, trimethyl acetic acid, caproic acid, β-trimethyl propinoic acid, heptanoic acid, caprylic acid, pelarginic acid, capric acid, undecylic acid, lauric acid, myristic acid, palmitic acid and stearic acid; alkenoic acids such as undecylenic acid and oleic acid; cycloalkyl carboxylic acids such as cyclopentyl carboxylic acid, cyclopropyl carboxylic acid, cyclobutyl carboxylic acid and cyclohexyl carboxylic acid; cycloalkyl alkanoic acids such as cyclopentyl acetic acid, cyclohexyl acetic acid, cyclopentyl propionic acid and cyclohexyl propionic acid; arylalkanoic acids such as phenyl acetic acid and phenyl propionic acid; aryl carboxylic acids such as benzoic acid and 2,4-dini-trobenzoic acid; phenoxy alkanoic acids such as phenoxy acetic acid; p-chlorophenoxy acetic acid, 2,4-dichlorophenoxy acetic acid, 4-terbutylphenoxy acetic acid, 3-phenoxy propinoic acid and 4-phenoxy butyric acid; heterocyclic carboxylic acids such as furane-2-carboxylic acid, 5-ter-butylfurane-2-carboxylic acid, 5-bromofurane-2-carboxylic acid and nicotinic acids; amino acids such as diethylaminoacetic acid and aspartic acid.

Example of chlorine-inert organic solvents are hydrocarbons and chlorinated hydrocarbons such as chloroform, methylene chloride, ethylene chloride, carbon tetrachloride, etc. and the amount of solvent used is selected so that an easily stirrable mixture is obtained. Generally, 250 ml of a hydrocarbon halide is used per mole of indoline.

Examples of suitable basic agents are alkali metal acetates such as sodium acetate, alkaline earth metal acetates such as calcium acetate, alkali metal hydroxides such as sodium hydroxide or potassium hydroxide, alkaline earth metal oxides or hydroxides such as magnesium oxide or calcium hydroxide, alkali metal carbonates such as sodium carbonates, alkaline earth metal carbonates such as calcium carbonates, alkali metal bicarbonates and alkaline earth metal bicarbonates such as sodium bicarbonate and magnesium hydroxide carbonate.

The amount of base used is at least equivalent to the molar amounts of acylating agent and chlorine, preferably 1:1.1:1.1:1.1. The amount of base or acylating agent may be greater but results in no advantage. Increased amounts of chlorine lead to a reduction in yield.

The base and water show a clear effect when they are both present and in the absence of water, the yield decreases by approximately 20%. The amount of water may vary within wide limits but normally 50 to 100 ml of water per equivalent of base is used as larger amounts of water has no advantage.

After separation of the aqueous phase, the organic phase containing 5-chloro-1-acyl-indoline may be evaporated to dryness followed by crystallization from a lower alkanol such as methanol, isopropanol or sec.-butanol, i.e. about 150 to 400 ml of alkanol, preferably isopropanol, per mole of indoline which results in yields of 76 to 85%.

The conversion of 5-chloro-1-acyl-indoline to 5-chloro-indoline may be effected in known manner by acid or alkaline saponification [see R. Ivan et al., Israel J. Chem., Vol. 2 (2), 37–42 (1964), Japanese Patent Application Ser. No. P 69 27 967]. The conversion to 5-chloro-indoline is effected in known manner by acid saponification e.g. with hydrochloric acid or preferably alkaline saponification of an alcohol solution, preferably isopropanolic solution, of 5-chloro-1-acyl-indoline. The excess of base which is preferably sodium hydroxide may be 100%. After distillation of the alcohol, treatment of the residue with water and chloroform and distillation of chloroform, the crude 5-chloro-indoline obtained may be purified by distillation, preferably in vacuum with a yield of 76–80% of theory based on indoline.

5-chloro-indole may be obtained from 5-chloro-indoline by reacting 5-chloro-indoline in the presence of finely-divided metallic ruthenium, optionally on a carrier in an organic solvent which is water-immiscible and elimination of water of reaction with a compound of the formula

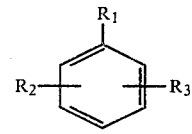

wherein $R_1$ is selected from the group consisting of —H,—OH,—CH$_3$,—C$_2$H$_5$, and —OCH$_3$, $R_2$ is —NO$_2$ and $R_3$ is selected from the group consisting of —H and —NO$_2$, at temperatures of 130° to 150° C., and working it up in known manner.

Despite the amines formed during the reaction from the nitrocompounds, the chlorine removal from the heterocycle by the metallic ruthenium is not catalyzed which is surprising. Suitable water-immiscible solvents are aromatic hydrocarbons such as toluene, xylene and mesitylene, halogenated aromatic hydrocarbons such as chlorobenzene, mixtures of aliphatic and aromatic hydrocarbons such as white spirit, and ethers such as anisol or dibutyl ether or mixtures thereof. The reaction velocity at 100°–110° C. is sufficiently high, and attains its maximum at 130°–160° C.

Suitable catalysts include metallic powdered ruthenium or the generally used combination of ruthenium metal on a carrier material such as carbon, Al$_2$O$_3$, silica gel or barium sulfate, where the metal portion is usually 5% by weight; higher concentrations (e.g. 10%) can also be used, but they bring no advantage and they only reduce the reaction time. Of particular advantage is the use of 7.5–10 g of the commercial carrier catalyst per mole of 5-chloro-indoline and in the range of 130°–160° C., the reaction is sufficiently fast. The catalyst may be separated in a simple manner by filtration, and can be regenerated. Taking into the account the reaction course, the workup, and the volumeric yield, an amount of 250 ml of solvent per mole of 5chloro-indoline was found to be of advantage. For the conversion to 5-chloro-indole, the oxidant may be used in amount of up to 5% in excess of the amount theoretically necessary such as nitrobenzene. Larger amounts are not harmful, but have no advantage either. The absence of a nitrocompound as a hydrogen acceptor leads to slower reaction and to considerable separation of chlorine with formation of the undesired indole.

In the following examples there are described several preferred embodiments to illustrate the invention. However, it should be understood that the invention is not intended to be limited to the specific embodiments.

5-CHLORO-INDOLE PREPARATION

STATE OF THE ART

DOS Nos. 2,618,152, 2,719,294 and 2,738,646 describe the use of 5-chloro-indole as an antidepressent, anti-emetic agent and anti-parkinson agent and U.S. Pat. No. 4,005,206 and German Pat. No. 1,143,823 describe the use of 5-chloro-indole as a starting material for 5-chloro-tryptamine which is an intermediate for the synthesis of tranquilizers and anti-hypertension agents. Intermediates 5-chloro-indoline and 5-chloro-1-acyl-indolines are also valuable starting materials for the preparation of other medicaments and 1-acetyl-5-chloro-indoline has phytotoxic activity as taught by Mazza et al. [Farmaco, Ed. Sci., Vol. 52 (1) (1977), p. 54]. However, direct synthesis of 5-chloro-indole by the steps of 1-acyl-indoline, 1-acyl-5-chloro-indoline and 5-chloro-indoline is not known.

Japanese Patent Application Serial No. 77-108,969 filed in 1977 [Chem. Abs., Vol. 88 (1978), p. 136451x] describes the preparation of indoline and benzene ring-substituted indolines by heating corresponding substituted 2-(o-aminoaryl)-ethanols up to 250° C. and Huisgen et al. [Chem. Ber., Vol. 93 (1960), p. 1496–1506] describe the preparation of indoline derivatives by cyclizing arine intermediates. Ikan et al. [Israel J. Chem., Vol. 2 (2) (1964), p. 37–42] describes the preparation of 5-chloro-indoline from indoline in several stages by nitrating the N-acetyl-indoline in the 5-position, reducing the nitro group to an amino group and subjecting the latter to exchange with chlorine by the Sandmeyer reaction followed by saponification of the acetyl group for a 35% yield of 5-chloro-indoline.

Gall et al. [J. Org. Chem., Vol. 20 (1955), p. 1538] describes the direct bromination of 1-acetyl-indoline in glacial acetic acid with bromine followed by saponification to obtain 5-bromo-indoline in 85% yield but attempts to repeat the process with chlorine results in only about a 45% yield of 5-chloro-1-acetyl-indoline. The latter result is not surprising in view of references such as Thesing et al. [Chem. Ber., Vol. 95 (1962), p. 2205], German Pat. No. 1,123,668, British Pat. No. 919,864 and the Chemistry of Heterocyclic Compounds, Vol. 25, Indoles, part II, Wiley Interscience, New York, London, Sidney, Toronto, 1972 p. 129 which teach that the reaction of N-acetylated-indoline-2-sulfonates in glacical acetic acid with chlorine, hypochlorous acid or alkali metal hypochlorites results in a variety of chlorinated products including 5- and 7-chloro compounds. Japanese Patent Application Ser. No. P 69-27967 (1969) teaches that these difficulties may be avoided by reacting 1-acetyl-indoline with N-chlorosuccinimide in carbon tetrachloride.

All these known methods are unsatisfactory for the commercial production of 5-chloro-1-acyl-indolines and/or 5-chloro-indoline by saponification of the acyl group due to poor yields and the use of rather expensive reagents such as N-chlorosuccinimide.

Ikan et al. [Israel J. of Chemistry, Vol. 2 (1964), p. 37–42] and Terent'ev et al. [Proc. Acad. Sci. USSR, Vol. 118 (2) (1958), p. 49–52] describe the dehydration of 5-chloro-indoline with chloranil to obtain 5-chloro-indole but due to the expense of chloranil, the process is not commercially feasible. French Pat. No. 1,576,807, DOS No. 1,770,977, Chem. Abs., Vol. 72 (1970), p. 121360n and Bader et al. [J.A.C.S., Vol. 83 (1961), p. 3319] tried to avoid this difficulty with partial success by heating indoline and its derivatives to high temperatures in the presence of palladium, platinum of Raney nickel catalysts, sometimes in the presence of a hydrogen acceptor. For example, indoline can be dehydrated at 100 to 150° C. in aromatics with a good yield of indole with hydrogen in the presence of finely divided palladium. Hunt et al. [J. Chem. Soc., (C) (1966), p. 344–345] teach reacting 5-methoxy-indoline in refluxing mesitylene in the presence of palladized carbon to obtain a 90% yield of 5-methoxy-indole.

Bakke [Acta, Chem. Scand., Vol. 28 (1974) No. 1, p. 134] describes reacting 4-chloro-indoline and 6-chloro-indoline with palladized carbon in a refluxing aromatic to obtain yields of 52% of 4-chloro-indole and 73% of 6-chloro-indole, respectively. However, the said process can not be used to convert 5-chloro-indoline to 5-chloro-indole since hydrogen and chlorine are both removed resulting in resinification to form undefined and non-distillable residues.

Org. Chem., Vol. 42 (3) (1977), p. 431 and Chemistry Letters, 1976, p. 655–656 describe the reaction of indoline in an aromatic solvent with nitrocompounds such as nitrobenzene in the presence of platinum group metal salts such as halides of rhodium, palladium or ruthenium at 100° C. to form indole, water and the amino compound corresponding to the starting nitrocompound. However, the presence of the platinum group metal salts causes to various degrees the removal of any halogen substituent and bases as they are formed increase this effect even more (Chemistry Letters, 1974, p. 855–856). Moreover, the solubility of the platinum group metal salts makes their recovery and subsequent reuse difficult and complicated.

OBJECTS OF THE INVENTION

It is an object of the invention to provide an economical process for the production of 5-chloro-indole starting from indoline in high yields.

It is another object of the invention to form 5-chloro-indole from indoline in a minimum number of steps in a commerically feasible process.

These and other objects and advantages of the invention will become obvious from the following detailed description.

THE INVENTION

The novel process of the invention for the preparation of 5-chloro-indole comprises reacting indoline in a chlorine-inert organic solvent with an acylating agent of an organic carboxylic acid to obtain the corresponding 1-acyl-indoline, reacting the latter in the presence of water and a basic agent with chlorine to form 5-chloro-1-acyl-indoline, subjecting the latter to saponification to obtain 5-chloro-indoline and reacting the latter in a water-immiscible organic solvent by heating with an aromatic nitrocompound in the presence of a finely powdered ruthenium catalyst to form 5-chloro-indole.

The acylating agent is preferably the carboxylic acid halide or acid anhydride with a molar ratio of indoline to acylating agent of 1:1 to 1.5 and the preferred reaction temperature is 0° to 60° C. The chlorination of the resulting 1-acyl-indoline after treatment with water in the presence of a base is effected with a molar ratio of 1-acyl-indoline to chlorine of 1:1 to 1.2 preferably at 0° to 60° C., most preferably 20° to 30° C. The organic solvent is then preferably distilled off and the 5-chloro-1-acyl-indoline is crystallized from a lower-alkanol of 1 to 6 carbon atoms which is unexpected in view of the state of the art.

Examples of suitable carboxylic acids of 1 to 18 carbon atoms for the process are alkanoic acid such as formic acid, acetic acid, propionic acid, butyric acid, isobutyric acid, valeric acid, isovaleric acid, trimethyl acetic acid, caproic acid, β-trimethyl propinoic acid, heptanoic acid, caprylic acid, pelarginic acid, capric acid, undecylic acid, lauric acid, myristic acid, palmitic acid and stearic acid; alkenoic acids such as undecylenic acid and oleic acid; cycloalkyl carboxylic acids such as cyclopentyl carboxylic acid, cyclopropyl carboxylic acid, cyclobutyl carboxylic acid and cyclohexyl carboxylic acid; cycloalkyl alkanoic acids such as cyclopentyl acetic acid, cyclohexyl acetic acid, cyclopentyl propionic acid and cyclohexyl propionic acid; arylalkanoic acids such as phenyl acetic acid and phenyl propionic acid; aryl carboxylic acids such as benzoic acid and 2,4-dini-trobenzoic acid; phenoxy alkanoic acids such as phenoxy acetic acid; p-chlorophenoxy acetic acid, 2,4-dichlorophenoxy acetic acid, 4-terbutylphenoxy acetic acid, 3-phenoxy propinoic acid and 4-phenoxy butyric acid; heterocyclic carboxylic acids such as furane-2-carboxylic acid, 5-ter-butylfurane-2-carboxylic acid, 5-bromofurane-2-carboxylic acid and nicotinic acids; amino acids such as diethylaminoacetic acid and aspartic acid.

Example of chlorine-inert organic solvents are hydrocarbons and chlorinated hydrocarbons such as chloroform, methylene chloride, ethylene chloride, carbon tetrachloride, etc. and the amount of solvent used is selected so that an easily stirrable mixture is obtained. Generally, 250 ml of a hydrocarbon halide is used per mole of indoline.

Examples of suitable basic agents are alkali metal acetates such as sodium acetate, alkaline earth metal acetates such as calcium acetate, alkali metal hydroxides such as sodium hydroxide or potassium hydroxide, alkaline earth metal oxides or hydroxides such as magnesium oxide or calcium hydroxide, alkali metal carbonates such as sodium carbonates, alkaline earth metal carbonates such as calcium carbonates, alkali metal bicarbonates and alkaline earth metal bicarbonates such as sodium bicarbonate and magnesium hydroxide carbonate.

The amount of base used is at least equivalent to the molar amounts of acylating agent and chlorine, preferably 1:1.1:1.1:1.1. The amount of base or acylating agent may be greater but results in no advantage. Increased amounts of chlorine lead to a reduction in yield.

The base and water show a clear effect when they are both present and in the absence of water, the yield decreases by approximately 20%. The amount of water may vary within wide limits but normally 50 to 100 ml of water per equivalent of base is used as larger amounts of water has no advantage.

After separation of the aqueous phase, the organic phase containing 5-chloro-1-acyl-indoline may be evaporated to dryness followed by crystallization from a lower alkanol such as methanol, isopropanol or sec.-butanol, i.e. about 150 to 400 ml of alkanol, preferably isopropanol, per mole of indoline which results in yields of 76 to 85%.

The conversion of 5-chloro-1-acyl-indoline to 5-chloro-indoline may be effected in known manner by acid or alkaline saponification [see R. Ivan et al., Israel J. Chem., Vol. 2 (2), 37–42 (1964), Japanese Patent Application Ser. No. P 69 27 967]. The conversion to 5-chloro-indoline is effected in known manner by acid saponification e.g. with hydrochloric acid or preferably alkaline saponification of an alcohol solution, preferably isopropanolic solution, of 5-chloro-1-acyl-indoline. The excess of base which is preferably sodium hydroxide may be 100%. After distillation of the alcohol, treatment of the residue with water and chloroform and distillation of chloroform, the crude 5-chloro-indoline obtained may be purified by distillation, preferably in vacuum with a yield of 76–80% of theory based on indoline.

5-chloro-indole may be obtained from 5-chloro-indoline by reacting 5-chloro-indoline in the presence of finely-divided metallic ruthenium, optionally on a carrier in an organic solvent which is water-immiscible and elimination of water of reaction with a compound of the formula

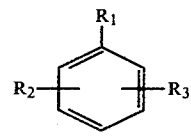

wherein $R_1$ is selected from the group consisting of —H, —OH, —CH$_3$, —C$_2$H$_5$, and —OCH$_3$, $R_2$ is —NO$_2$ and $R_3$ is selected from the group consisting of —H and —NO$_2$, at temperatures of 130° to 150° C., and working it up in known manner.

Despite the amines formed during the reaction from the nitrocompounds, the chlorine removal from the heterocycle by the metallic ruthenium is not catalyzed which is surprising. Suitable water-immiscible solvents are aromatic hydrocarbons such as toluene, xylene and mesitylene, halogenated aromatic hydrocarbons such as chlorobenzene, mixtures of aliphatic and aromatic hydrocarbons such as white spirit, and ethers such as anisol or dibutyl ether or mixtures thereof. The reaction velocity at 100°–110° C. is sufficiently high, and attains its maximum at 130°–160° C.

Suitable catalysts include metallic powdered ruthenium or the generally used combination of ruthenium metal on a carrier material such as carbon, Al$_2$O$_3$, silica gel or barium sulfate, where the metal portion is usually 5% by weight; higher concentrations (e.g. 10%) can also be used, but they bring no advantage and they only reduce the reaction time. Of particular advantage is the use of 7.5–10 g of the commercial carrier catalyst per mole of 5-chloro-indoline and in the range of 130°–160° C., the reaction is sufficiently fast. The catalyst may be separated in a simple manner by filtration, and can be regenerated. Taking into the account the reaction course, the workup, and the volumeric yield, an amount of 250 ml of solvent per mole of 5chloro-indoline was found to be of advantage. For the conversion to 5-chloro-indole, the oxidant may be used in amount of up to 5% in excess of the amount theoretically necessary such as nitrobenzene. Larger amounts are not harmful, but have no advantage either. The absence of a nitrocompound as a hydrogen acceptor leads to slower reaction and to considerable separation of chlorine with formation of the undesired indole.

In the following examples there are described several preferred embodiments to illustrate the invention. However, it should be understood that the invention is not intended to be limited to the specific embodiments.

EXAMPLE 1

5-chloro-indoline 1428 g (12 moles) of indoline and 3000 ml of chloroform were admixed with stirring with 1350 g (132 moles) of acetic acid anhydride with cooling to keep the temperature at 20° to 30° C. and the mixture was stirred for one hour. Then, 600 ml of water were added thereto followed by addition in portions over 7½ hours to the mixture of 702 g (6.6 moles) of sodium carbonate with vigorous stirring and external cooling during which carbon dioxide evolved. Within 7.5 hours 937 g (13.2 moles) of chlorine were added to the mixture held at no more than 30° C. and the mixture was stirred for 30 minutes. 3000 g of water were added to the mixture which was stirred for 15 minutes after which the organic phase was separated and evaporated to dryness under reduced pressure at 130° C. At 70° to 75° C. 2400 ml of isopropanol were added to the residue and the mixture was stirred with heating until total dissolution occured and the mixture was cooled to room temperature and was stirred at 20° to 25° C. for one hour. The mixture was vacuum filtered to obtain 5-chloro-1-acetyl-indoline melting at 115° to 116° C. which was washed with 1500 ml of isopropanol.

The said product was admixed with 4600 ml of isopropanol and the mixture was heated to reflux with stirring after which 962 ml (18.4 moles) of aqueous 50% sodium hydroxide solution were added thereto with stirring. The mixture was refluxed with stirring for 12 hours during which sodium acetate precipitated. The alcohol was then distilled and recycled for the next process. To the residue was added 4500 ml of water and 1500 ml of chloroform and the mixture was throughly stirred. The decanted organic phase was freed of chloroform by distillation under a water jet vacuum at 120° C. The residue was distilled under reduced pressure to obtain 1400 to 1475 g (76–80% yield) of 5-chloro-indoline with a boiling point of 148°–152° C. at 19 mbar in the form of a water-clear liquid which turned brown after standing in light and air. The isopropanol could be replaced by ethanol or sec.-butanol.

EXAMPLE 2

The procedure of Example 1 was repeated using as the base 1800 g (13.2 moles) of sodium acetate trihydrate and an acylation and chlorination temperature of 25° C. to obtain a 76% to 80% yield of 5-chloro-indoline.

EXAMPLE 3

The procedure of Example 1 was repeated using as the base 1,050 g (6.6 moles) of calcium acetate and an acylation and chlorination temperature of 35° C. to obtain a 75–77% yield of 5-chloro-indoline.

EXAMPLE 4

The procedure of Example 1 was repeated using as the base 528 g (13.2 moles) of sodium hydroxide and an acylation and chlorination temperature of 40° C. for a 74–76% yield of 5-chloro-indoline.

EXAMPLE 5

The procedure of Example 1 was repeated using as the base 741 g (13.2 moles) of potassium hydroxide and an acylation and chlorination temperature of 25° C. for a 76–80% yield of 5-chloro-indoline.

EXAMPLE 6

The procedure of Example 1 was repeated using as the base 266 g (6.6 moles) of magnesium oxide and an acylation and chlorination temperature of 25° C. for a 76–78% yield of 5-chloro-indoline.

EXAMPLE 7

The procedure of Example 1 as repeated using as the base 490 g (6.6 moles) of calcium hydroxide and an acylation and chlorination temperature of 30° C. for a 75–78% yield of 5-chloro-indoline.

EXAMPLE 8

The procedure of Example 1 was repeated using as the base 370 g (6.6 moles) of calcium oxide and an acylation and chlorination temperature of 25° C. for a 76–78% yield of 5-chloro-indoline.

EXAMPLE 9

The procedure of Example 1 was repeated using as the base 702 g (6.6 moles) of sodium carbonate and an acylation and chlorination temperature of 60° C. for a 70–73% yield of 5-chloro-indoline.

EXAMPLE 10

The procedure of Example 1 was repeated using as the base 660 g (6.6 moles) of calcium carbonate and an acylation and chlorination temperature of 30° C. for a 75–77% yield of 5-chloro-indoline.

EXAMPLE 11

The procedure of Example 1 was repeated using as the base 1,110 g (13.2 moles) of sodium bicarbonate and an acylation and chlorination temperature of 5° C. for a 74–77% yield of 5-chloro-indoline.

EXAMPLE 12

The procedure of Example 1 was repeated using as the base 1,320 g (13.2 moles) of potassium bicarbonate and an acylation and chlorination temperature of 0° C. for a 74–77% yield of 5-chloro-indoline.

EXAMPLE 13

The procedure of Example 1 was repeated using as the base 608 g (13.2 moles) of magnesium hydroxide carbonate (4 $MgCO_3.Mg(OH)_2.4H_2O$) and an acylation and chlorination temperature of 25° C. for a 74–77% yield of 5-chloro-indoline.

EXAMPLE 14

The procedure of Example 1 was repeated using 1,636 g (16 moles) of acetic acid anhydride and 851 g (8 moles) of sodium carbonate in 730 ml of water to obtain 1,420 g (77% yield) of 5-chloro-indoline.

EXAMPLE 15

The procedure of Example 1 was repeated using 851 g (8 moles) of sodium carbonate, 730 ml of water and 1136 g (16 moles) of chlorine to obtain 1180 g (64% yield) of 5-chloro-indoline.

EXAMPLE 16

The procedure of Example 1 was repeated using 702 g (6.6 moles) of sodium carbonate and no water to obtain 1106 g (60% yield) of 5-chloro-indoline.

EXAMPLE 17

The procedure of Example 1 was repeated using 1500 ml of water before the sodium carbonate addition to obtain 1,410 g (76.5% yield) of 5-chloro-indoline.

EXAMPLE 18

The procedure of Example 1 was repeated using 600 ml of water and no base to obtain 1,106 g (60% yield) of 5-chloro-indoline.

EXAMPLE 19

The procedure of Example 1 was repeated with no water addition and no base to obtain 980.5 g (53.2% yield) of 5-chloro-indoline.

EXAMPLE 20

A mixture of 714 g (6 moles) of indoline and 1500 ml of chloroform and 528 g (6.6 moles) of aqueous sodium hydroxide solution (50%) was stirred at 20° to 30° C. while adding 928 g (6.6 moles) of benzoyl chloride thereto and the mixture was stirred for one hour after which 300 ml of water and 351 g (3.3 moles) of sodium carbonate were added thereto. 468.5 g (6.6 moles) of chlorine were added to the mixture with vigorous stirring and water cooling over 5½ hours to keep the temperature below 30° C. The mixture was stirred for 30 minutes and after the addition of 1500 ml of water, the mixture was stirred for 15 minutes. The decanted organic phase was evaporated to dryness under reduced pressure at 130° C. and the residue was taken up in 1200 ml of isopropanol. The mixture was heated with stirring until complete dissolution occured and the mixture was cooled and stirred at 20°–25° C. for one hour. The mixture was vacuum filtered to obtain 5-chloro-1-benzoyl-indoline melting at 135°–136° C.

The said product was washed with 750 ml of isopropanol and was then added to 2300 ml of sec.-butanol. The mixture was refluxed with stirring while adding dropwise thereto 481 ml of 50% aqueous sodium hydroxide (9.2 moles) solution and the mixture was refluxed with stirring for 12 hours. The alcohol was distilled off and the residue was added to a mixture of 3000 ml of water and 750 ml of chloroform. The mixture was stirred well and the decanted organic phase was distilled to remove chloroform. The residue was distilled under reduced pressure at 120°–130° C. to obtain 700 g (76% yield) of 5-chloro-indoline with a boiling point of 148°–152° C. at 19 mbar.

EXAMPLE 21

The procedure of Example 1 was repeated using 6 moles of indoline and 860 g (6.6 moles) of propionic acid anhydride to obtain 710 g (77% yield) of 5-chloro-indoline.

EXAMPLE 22

The procedure of Example 20 was repeated using 899.5 g (6.6 moles) of hexanoyl chloride to obtain 738 g (80% yield) of 5-chloro-indoline.

EXAMPLE 23

The procedure of Example 20 was repeated using 1020 g (6.6 moles) of phenylacetyl chloride to obtain 728 g (79% yield) of 5-chloro-indoline.

EXAMPLE 24

The procedure of Example 20 was repeated using 518 g (6.6 moles) of acetyl chloride or 812 g (6.6 moles) of acetyl bromide to obtain 719 g (78% yield) of 5-chloro-indoline.

EXAMPLE 25

The procedure of Example 20 was repeated using 610.5 g (6.6 moles) of propionic acid chloride to obtain 700 g (76% yield) of 5-chloro-indoline.

EXAMPLE 26

The procedure of Example 20 was repeated using 1020 g (6.6 moles) of cyclohexane-1,2-dicarboxylic acid anhydride to obtain 705 g (76.5% yield) of 5-chloro-indoline.

EXAMPLE 27

The procedure of Example 1 was repeated using 978 g (6.6 moles) of phthalic anydride to obtain 709 g (77% yield) of 5-chloro-indoline.

EXAMPLE 28

The procedure of Example 1 was repeated using 660.5 g (6.6 moles) of succinic acid anhydride to obtain 737 g (80% yield) of 5-chloro-indoline.

EXAMPLE 29

For comparative purposes, the process of Gall et al. [J. Org. Chem., Vol. 20 (1955), p. 1541] was used to prepare 5-chloro-indoline as follows.

74.5 g (1.05 moles) of chlorine were added with stirring at 20° to 30° C. to a mixture of 161 g (1 mole) of 1-acetyl-indoline in 1,050 ml of glacial acetic acid and the mixture was stirred for 15 minutes after which 8500 ml of water were added thereto with stirring. The mixture was stirred for 30 minutes and sodium bisulfite was added to destroy excess chlorine and was then vacuum filtered. The recovered product was dissolved in 250 ml of hot isopropanol and the mixture was cooled with stirring and then vacuum filtered. The product was rinsed with 250 ml of isopropanol to obtain 5-chloro-1-acetyl-indoline which was saponified as in Example 1 to obtain 70 g (45% yield) of 5-chloro-indoline.

EXAMPLE 30

5-chloro-indole

A mixture of 2000 ml of xylene, 1228 g (8 moles) of 5-chloro-indoline, 344 g (2.79 moles) of nitrobenzene and 60 g of 5% ruthenium on carbon catalyst was refluxed with stirring for 6 to 7 hours while distilling off 96 ml of water during which the temperature rose to 148°–150° C. The mixture was cooled to room temperature and was vacuum filtered. The filter was washed with 300 ml of xylene and the filtrate was stirred three times for 10 minutes each time with 800 ml of dilute hydrochloric acid formed by diluting 400 ml of concentrated hydrochloric acid with 2000 ml of water to remove the formed aniline. The organic phase was dried with 150 to 200 g of potassium carbonate and was evaporated to dryness under reduced pressure at 140° C. The residue was subjected to fractional distillation to obtain a first fraction of 70 g (6% yield) of product with a boiling point of 100° to 105° C. at 0.04 mbar, a second fraction of 990 to 1048 g (85–90% yield) of 5-chloro-indole with a boiling point of 105° to 110° C. at 0.04 mbar and a melting point of 70° to 72° C. and a residue of 75 g (about 6.4% yield). The second fraction was solidied and was ground as abeige to white powder.

EXAMPLES 31 TO 51

Using the procedure of Example 30, 5-chloro-indoline was reacted using the solvent, oxidizing agent and catalyst listed in the following Table to obtain the indicated yields of 5-chloro-indole.

TABLE I

| Example No. | Solvent | Oxidizing Agent | Catalyst | % yield of 5-chloro-indole |
|---|---|---|---|---|
| 31 | xylene | 2-nitroanisol | Ru/C (5%) | 85 |
| 32 | xylene | 4-nitrophenol | Ru/C (5%) | 79 |
| 33 | xylene | 4-nitrotoluene | Ru/C (5%) | 87 |
| 34 | xylene | 1,3-dinitrobenzene | Ru/C (5%) | 81 |
| 35 | xylene | 2,4-dinitrotoluene | Ru/C (5%) | 80 |
| 36 | xylene | nitrobenzene | Ru/Al$_2$O$_3$ (5%) | 88 |
| 37 | xylene | nitrobenzene | Ru/BaSO$_4$ (5%) | 90 |
| 38 | xylene | nitrobenzene | Ru (ground) | 85 |
| 39 | xylene | nitrobenzene | Ru/C (10%) | 87[1] |
| 40 | xylene | nitrobenzene | Ru/C (5%) | 90[2] |
| 41 | xylene | nitrobenzene | Ru/C (5%) | 70[3] |
| 42 | xylene | nitrobenzene | Ru/C (5%) | 83[4] |
| 43 | xylene | nitrobenzene (20% excess) | Ru/C (5%) | 87 |
| 44 | chlorobenzene | nitrobenzene | Ru/C (5%) | 90 |
| 45 | dibutylether | nitrobenzene | Ru/C (5%) | 84 |
| 46 | mesitylene | nitrobenzene | Ru/C (5%) | 86 |
| 47 | white spirit | nitrobenzene | Ru/C (5%) | 86 |
| 48 | anisol | nitrobenzene | Ru/C (5%) | 87 |
| 49 | toluene | nitrobenzene | Ru/C (5%) | 79[5] |
| 50 | xylene | nitrobenzene equiv. Menge | Ru/C (5%) | 84.5 |
| 51 | xylene | nitrobenzene 20% excess | Ru/C (5%) | 88 |

[1] Reduction of reaction time by 10%
[2] Reduction of reaction time by 10% and double amount of catalyst as in 30
[3] Half amount of catalyst as in 30
[4] ⅔ of amount of catalyst as in 30
[5] Extension of reaction time by 50%.

EXAMPLE 52

As a comparison example, 153.6 g of 5-chloro-indoline, 15 g of 5% palladized carbon and 500 ml of xylene were refluxed and stirred until gas evolution ceased. After separation of the catalyst and evaporation of the solvent, a dark, viscous undistillable residue was obtained which was soluble in acetone.

EXAMPLE 53

As another comparison example, Example 30 was repeated with a 5% palladized carbon catalyst which resulted in about 25% yield of a distillate with a boiling point of 91° to 110° C. at 0.04 mbar which contained about 70% 5-chloro-indole. The remainder of the product was a foul smelling undistillable resin soluble in acetone.

EXAMPLE 54

In an another comparison example, Example 30 was repeated using a 5% rhodium-carbon catalyst to obtain a second fraction of a 80 to 83% yield of a product with a boiling point of 88° to 105° C. at 0.04 mbar which was about 65 to 68% of 5-chloro-indole with the remainder being indole which means a considerable removal of chlorine.

EXAMPLE 55

In another comparison example in which 5% ruthenium-carbon catalyst without a nitrocompound as the hydrogen acceptor was used, a mixture of 307.2 g (2 moles) of 5-chloro-indoline, 500 ml of xylene and 15 g of 5% ruthenium-carbon catalyst was refluxed with stirring for 7 hours and the mixture was then cooled and vacuum filtered. 800 ml of dilute hydrochloric acid formed from 130 ml of concentrated hydrochloric acid and 670 ml of water was added in 3 equal portions to the filtrate. The organic phase was dried over potassium carbonate and was evaporated to dryness under reduced pressure. The residue was subjected to fractional distillation to obtain a first fraction of 146 g of a product with a boiling point of 92° to 98° C. at 0.03 mbar and a melting point of 57° to 60° C. and a residue of 12 g (4% yield). Gas chromatography of the first fraction indicated that it was a mixture of 35% of indole and 65% of 5-chloro-indole. The acid extract was neutralized to recover 132 g (42.8% yield) of 5-chloro-indoline.

Various modification of the process of the invention may be made without departing from the spirit or scope thereof and it should be understood that the invention is intended to be limited only as defined in the appended claims.

What we claim is:

1. A process for the preparation of 5-chloro-indole comprising reacting indoline in a chlorine-inert organic solvent with an acylating agent of an organic carboxylic acid to obtain the corresponding 1-acyl-indoline, reacting the latter in the presence of water and a basic agent with chlorine to form 5-chloro-1-acyl-indoline, subjecting the latter to acid or alkaline saponification to obtain 5-chloro-indoline, and reacting the latter in a water-immiscible organic solvent by heating with an aromatic nitrocompound in the presence of a finely powdered ruthenium catalyst to form 5-chloro-indole.

2. The process of claim 1 wherein the acylation step and chlorination step are effected at 0° to 60° C. in an organic solvent selected from the group consisting of chloroform, carbon tetrachloride and ethylene chloride.

3. The process of claim 2 wherein the molar ratio of indoline to acylating agent is 1:1 to 1.5, the molar ratio of indoline to chlorine is 1:1 to 1.2 and the molar equivalent of indoline to acylating agent to base is 1:1.1:1.1:1.1.

4. The process of claim 1 or 2 or 3 wherein the base is selected from the group consisting of alkali metal hydroxides, acetates, carbonates and bicarbonates and alkaline earth metal oxides, hydroxides, acetates, carbonates and bicarbonates and alkaline earth metal hydroxide carbonates in about least molar equivalent amount to the acylating agent.

5. The process of claim 1 or 2 or 3 wherein 50 to 100 ml of water per mole of indoline is present in the chlorination step.

6. The process of claim 1, wherein the isolated 5-chloro-indoline is reacted at temperatures between 100° and 180° C. with a compound having the general formula

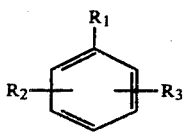

wherein $R_1$ is selected from the group consisting of —H, —OH, —$CH_3$—$C_2H_5$, and —$OCH_3$, $R_2$ is —$NO_2$ and $R_3$ is selected from the group consisting of —H and —$NO_2$, in the presence of finely powdered metallic ruthenium which may be on a carrier system in an organic solvent not miscible with the water under azeotropic distillation of water and wherein the 5-chloro-indole is separated by a known manner.

7. The process of claim 6 wherein the ruthenium catalyst is 5 to 10% by weight of ruthenium on a carrier selected from the group consisting of carbon, silica gel, aluminum oxide and barium sulfate.

8. The process of claim 6 or 7 wherein the ruthenium catalyst is 5% ruthenium on a carrier and 5 to 20 g of the catalyst are used per mole of 5-chloro-indoline.

9. The process of claim 6 or 7 wherein the 200–400 ml of water-immiscible solvent is present per mole of 5-chloro-indoline.

10. The process of claim 6 or 7 wherein the nitrocompounds are selected from the group consisting of 2-nitro-anisole, 4-nitro-anisole, 4-nitro-toluene, 1,3-dinitro-toluene and nitrobenzene.

* * * * *

UNITED STATES PATENT AND TRADEMARK OFFICE
CERTIFICATE OF CORRECTION

PATENT NO. : 4,377,699
DATED : March 22, 1983
INVENTOR(S) : MANFRED MAURER ET AL.

It is certified that error appears in the above—identified patent and that said Letters Patent is hereby corrected as shown below:

Title page [75]: "Kirchheim" should read
-- Kirchheim/Weinstr. --; and
"Hassloch" should read -- Hassloch/Pfalz --.
Column 1, line 17: "54[." should read -- 54]. --.
Column 2, line 2: second occurrence should read -- or --.
Column 2, line 62: After "60°C"
--, most preferably 20-30°C --.
Column 3, line 19: "dini-trobenzoic" should read
-- dinitrobenzoic --.
Column 4, line 55: "5chloro" should read -- 5-chloro --.
Column 6, line 1 of Example 7: "as repeated" should read
-- was repeated --.

Signed and Sealed this

Twenty-fourth Day of January 1984

[SEAL]

Attest:

GERALD J. MOSSINGHOFF

Attesting Officer   Commissioner of Patents and Trademarks